(12) United States Patent
Pedersen et al.

(10) Patent No.: US 12,151,089 B2
(45) Date of Patent: Nov. 26, 2024

(54) DRUG DELIVERY DEVICE HAVING DOSE INDICATOR

(71) Applicant: AMGEN INC., Thousand Oaks, CA (US)

(72) Inventors: Jakob Halkjaer Pedersen, Frederiksberg (DK); Matias Melander, Copenhagen (DK)

(73) Assignee: AMGEN INC., Thousand Oaks, CA (US)

( * ) Notice: Subject to any disclaimer, the term of this patent is extended or adjusted under 35 U.S.C. 154(b) by 752 days.

(21) Appl. No.: 17/273,663

(22) PCT Filed: Oct. 4, 2019

(86) PCT No.: PCT/US2019/054602
§ 371 (c)(1),
(2) Date: Mar. 4, 2021

(87) PCT Pub. No.: WO2020/072846
PCT Pub. Date: Apr. 9, 2020

(65) Prior Publication Data
US 2021/0338936 A1    Nov. 4, 2021

Related U.S. Application Data

(60) Provisional application No. 62/742,066, filed on Oct. 5, 2018.

(51) Int. Cl.
*A61M 5/315* (2006.01)
*A61M 5/20* (2006.01)

(52) U.S. Cl.
CPC ........ *A61M 5/3157* (2013.01); *A61M 5/2033* (2013.01); *A61M 5/31501* (2013.01);
(Continued)

(58) Field of Classification Search
CPC .. A61M 5/3157; A61M 5/31526; A61M 5/20; A61M 2205/581; A61M 2005/2013
See application file for complete search history.

(56) References Cited

U.S. PATENT DOCUMENTS

| | | | | |
|---|---|---|---|---|
| 8,721,593 | B2 * | 5/2014 | Wozencroft | ........ A61M 5/2033 604/189 |
| 2011/0077599 | A1 | 3/2011 | Wozencroft | |

(Continued)

FOREIGN PATENT DOCUMENTS

| | | |
|---|---|---|
| CN | 105327432 A | 2/2016 |
| CN | 107690338 A | 2/2018 |

(Continued)

OTHER PUBLICATIONS

Office Action received in counterpart Taiwanese Patent Application No. 108136060, dated Mar. 6, 2023.
(Continued)

*Primary Examiner* — Phillip A Gray (57) ABSTRACT

A drug delivery device includes a housing defining a shell having a proximal end and a distal end and a longitudinal axis extending between the proximal end and the distal end, a needle assembly at least partially disposed within the housing at the proximal end, a drive assembly at least partially disposed within the housing and operably coupled to the needle assembly, and an audible indicator operably coupled to the drive assembly. The needle assembly includes a syringe containing a medicament and a needle or a cannula. The drive assembly is movable between an initial position and a second position that results in the medicament being expelled from the syringe. Upon the drive assembly being positioned in the second position, the audible indicator engages the drive assembly to generate an audible sound indicating the medicament has been expelled from the syringe.

15 Claims, 7 Drawing Sheets

(52) U.S. Cl.
CPC . *A61M 5/31526* (2013.01); *A61M 2205/0216* (2013.01); *A61M 2205/0222* (2013.01); *A61M 2205/0272* (2013.01); *A61M 2205/43* (2013.01); *A61M 2205/581* (2013.01)

(56) References Cited

U.S. PATENT DOCUMENTS

| | | |
|---|---|---|
| 2013/0211330 A1 | 8/2013 | Pedersen et al. |
| 2015/0151053 A1 | 6/2015 | Holmqvist |
| 2016/0166772 A1* | 6/2016 | Mirzazadeh ...... A61M 5/31513 604/222 |
| 2017/0354779 A1 | 12/2017 | Atterbury et al. |
| 2018/0169342 A1 | 6/2018 | Mosebach et al. |

FOREIGN PATENT DOCUMENTS

| | | |
|---|---|---|
| JP | 2011520545 A | 7/2011 |
| JP | 2013534164 A | 9/2013 |
| JP | 2017534392 A | 11/2017 |
| TW | 201705996 A | 2/2017 |

OTHER PUBLICATIONS

Office Action received in counterpart Argentinian Patent Application No. P190102840, dated May 22, 2023.
Office Action received in counterpart Japanese Patent Application No. 2021-517943, dated Sep. 5, 2023.
International Search Report and Written Opinion for International Application No. PCT/US2019/054602, mailing date Dec. 13, 2019.
Office Action received in counterpart Japanese Patent Application No. 2021-517943, dated Mar. 5, 2024.
Second Office Action received in counterpart Argentinian Patent Application No. P190102840, dated Nov. 8, 2023.
Examination Report received in counterpart European Patent Application No. 19794299.8, dated Nov. 30, 2023.
Examination Report received in counterpart Australian Patent Application No. 2019355979, dated May 28, 2024.
Office Action received in counterpart Taiwanese Patent Application No. 112143925, dated Jul. 9, 2024.
Examination Report received in counterpart Australian Patent Application No. 2019355979, dated Sep. 20, 2024.

* cited by examiner

DRUG DELIVERY DEVICE HAVING DOSE INDICATOR

CROSS-REFERENCE TO RELATED APPLICATION

This is the United States national phase of International Patent Application No. PCT/2019/054602, filed Oct. 4, 2019, which application claims priority to U.S. Provisional Patent Application No. 62/742,066, filed Oct. 5, 2018, the entire contents of each of which are hereby incorporated by reference.

FIELD OF DISCLOSURE

The present disclosure generally relates to drug delivery devices and, more particularly, to construction and actuation of a dose indicator of a drug delivery device.

BACKGROUND

Drug delivery devices such as autoinjectors and on-body injectors offer several benefits in delivery of medicaments and/or therapeutics. One of the benefits can include simplicity of use, as compared with traditional methods of delivery using, for example, conventional syringes.

Autoinjectors may be used to deliver a number of different drugs having varying viscosities and/or desired volumes. Because of aversions to exposed needles, as well as health and safety issues that may be involved, various types of injectors and other devices have been developed for concealing needles from the user and automating the injection task to assist the user in performing the injection, ensure reliable delivery of the medication and ensure patient safety. Accordingly, many of these devices provide limited visual access to the inner workings of the devices due to their complexities and to ease user apprehensions. As a result, users may not be able to accurately identify a remaining quantity of medicament in the device, and thus they may preemptively remove the device from the injection site prior to administration of the full dose. Conversely, users may take an opposite approach where they hold the device against the injection site for excessively long periods of time to ensure the full dose was administered. Doing so may result in user discomfort, uncertainty, and/or unease.

SUMMARY

In accordance with a first aspect, a drug delivery device includes a housing defining a shell having a proximal end, a distal end, and a longitudinal axis extending between the proximal end and the distal end, a needle assembly at least partially disposed within the housing at the proximal end, a drive assembly at least partially disposed within the housing and operably coupled to the needle assembly, and an audible indicator operably coupled to the drive assembly. The needle assembly includes a syringe containing a medicament and a needle or a cannula. The drive assembly is movable between an initial position and a second position that results in the medicament being expelled from the syringe. Upon the drive assembly being positioned in the second position, the audible indicator engages the drive assembly to generate an audible sound indicating the medicament has been expelled from the syringe. In some forms, the audible indicator is additionally adapted to at least partially disengage from the drive assembly upon commencement of movement of the drive assembly from the first position towards the second position.

In some forms, the drive assembly includes a plunger rod having a first end, a second end, and a first detent positioned at the second end. The drive assembly may further include a second detent positioned at a distance between the first end and the second end.

In some examples, the audible indicator may be in the form of a resilient ring having an engagement tab. The audible indicator may be constructed from at least one of a polymer or a metallic material. The engagement tab is adapted to engage the first and/or the second detent of the plunger rod. In other examples, the drive assembly may additionally include a magnetic member, and the audible indicator may include a metallic member. In these examples, upon the drive assembly being positioned at the second position, the metallic member engages the magnetic member to generate the audible sound.

In some forms, the audible indicator may be in a relaxed configuration when the drive assembly is in the second position. Further, in some examples, the audible indicator may be in a relaxed configuration when the drive assembly is in the initial position.

In accordance with a second aspect, a drug delivery device includes a housing defining a shell having a proximal end, a distal end, and a longitudinal axis extending between the proximal end and the distal end, a needle assembly at least partially disposed within the housing at the proximal end, a drive assembly at least partially disposed within the housing and operably coupled to the needle assembly, and an audible indicator operably coupled to the drive assembly. The needle assembly includes a syringe containing a medicament and a needle or a cannula. The drive assembly is movable between an initial position and a second position that results in the medicament being expelled from the syringe. Upon completion of delivery of the medicament via the needle assembly, the audible indicator engages the drive assembly to generate an audible sound indicating the medicament has been expelled from the syringe

BRIEF DESCRIPTION OF THE DRAWINGS

The above needs are at least partially met through provision of the torque driven drug delivery device described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an injector includes a housing, a container or syringe assembly containing a medicament to be injected into a user, and a rotatable drive or actuating assembly that uses a torque spring to cause the medicament to be injected into a user. Upon completion of administration of the drug, an audible indicator provides a sound to indicate an end-of-dose.

Figure 1A:
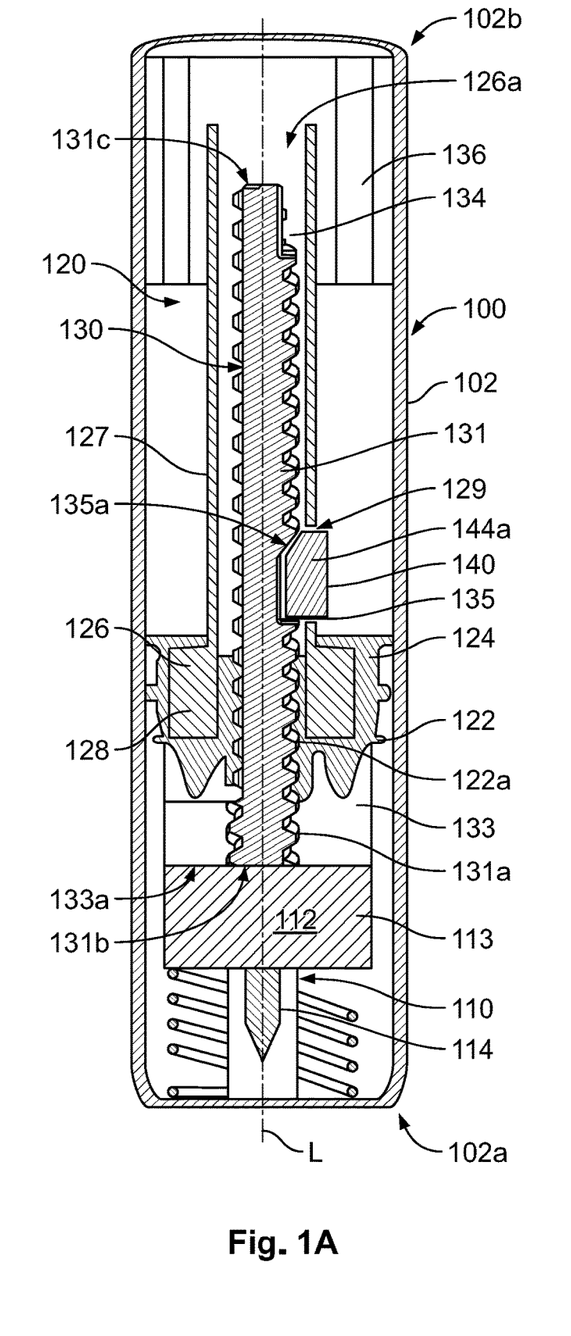
FIG. 1a illustrates a cross-sectional view of an example torque driven drug delivery device having an audible indicator in accordance with various embodiments.
Figure 1B:
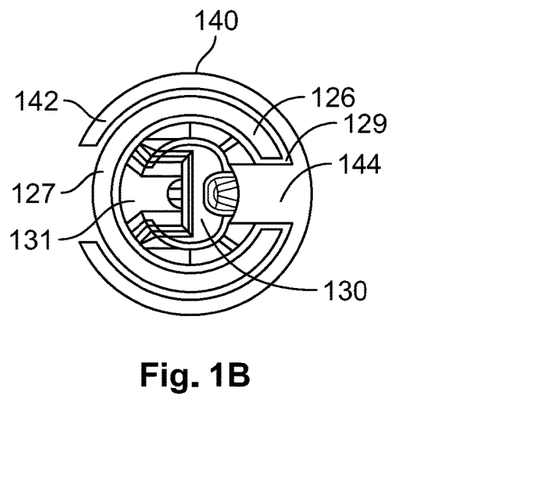
FIG. 1b illustrates a top plan cross-sectional view of a portion of the example drug delivery device of FIG. 1a depicting an audible indicator in a relaxed condition in accordance with various embodiments.

Referring now to the drawings, and in particular to FIGS. 1a and 1b, an example autoinjector 1000 is provided. The injector 100 is a simplified version of a typical device, and therefore does not illustrate all of the necessary components and/or features of a drug delivery device. The injector 100 includes a housing 102 defining a shell, a needle assembly 110 at least partially disposed within the shell 102, a drive assembly 120 also at least partially disposed within the shell 102, and an audible indicator 140 at least partially disposed within the shell 102. The shell 102 includes a proximal end 102a, a distal end 102b, and defines a longitudinal axis "L" extending between the proximal end 102a and the distal end 102b.

The needle assembly 110 is generally disposed at or near the proximal end 102a of the shell 102 and includes a syringe barrel 112 containing a medicament 113 and a needle or a cannula 114. The needle assembly 110 may include any number of additional components such as, for example, a sidewall or sidewalls, openings to allow the medicament 113 to pass to the needle or cannula 114, return springs, shield members, filter members, and the like, but for the sake of brevity, will not be discussed in substantial detail. A portion of the syringe barrel 112 may be open to accommodate a portion of the drive assembly 120, which will be described in further detail below. The syringe barrel 112 may be of any desired shape and/or size to accommodate various quantities of medicament 113. In some examples, the syringe barrel 112 can be constructed from a cyclic-olefin polymer ("COP"). Other examples are possible.

The drive assembly 120 may include any number of components that are movable between an initial position and a second position that result in the medicament 113 being expelled from the syringe barrel 112. For example, the drive assembly 120 may include a nut 122 positioned adjacent to the syringe barrel 112, a trigger ring 124, a plunger rod guide 126, a plunger rod assembly 130, and a drive mechanism in the form of a torque or power spring 136. Generally, portions of the drive assembly 120 may be fixedly coupled to the shell 102 via any number of approaches. In some arrangements, the nut 122 may be formed integrally with the shell 102 and may include a threaded opening 122a. The trigger ring 124 selectively engages the nut 122 and is configured to move in an axial direction. In the illustrated example, the trigger ring 124 is in the form of a generally cylindrical ring having a generally circular inner surface and any number of ledges, protrusions, and grooves disposed around and/or inside the circumference of the ring. The trigger ring 124 may be coupled to the housing 102 via any number of techniques.

The plunger rod guide 126 includes a rod portion 127, a base portion 128 coupled thereto, and a slot 129. The plunger rod guide 126 includes an opening 126a extending at least partially through the rod portion 127 and the base portion 128. The base portion 128 can have any number of projections or tabs extending therefrom to define a slidable engagement with the trigger ring 124.

The plunger rod assembly 130 includes a plunger rod 131 and a plunger 133 that are moveable along the longitudinal axis L of the housing 102. The plunger rod 131 has a threaded portion 131a which is threadably coupled to the plunger rod guide 126 and the threaded opening 122a of the nut 122. The plunger rod 131 extends between a first end 131b and a second end 131c which defines a first detent or cut out 134 which will be discussed in further detail below. The plunger rod 131 may additionally define a second detent or cut out 135 that is located at a distance between the first end 131b and the second end 131c. In some approaches, the plunger rod assembly 130 may further include a washer (not shown) that minimizes frictional losses between rotation of the plunger rod 131 and the non-rotating plunger 133 and also may be used to adjust the volume of medicament 113 based on the thickness of the washer. Accordingly, a range of fill volumes of medicament 113 may be used in the same device 100.

The rod portion 127 of the plunger rod guide 126 is coupled to the plunger rod assembly 130 via any number of approaches including, for example, via a splined connection or slotted arrangement that allows for the plunger rod assembly 130 to be axially displaced relative to the plunger rod guide 126. As such, the plunger rod guide 126 guides rotational movement of the plunger rod assembly 130. The threaded portion 131a of the plunger rod 131, and correspondingly, the threaded opening 122a of the nut 122 may have a thread pitch suitable for any desired drug delivery rate or force/torque combination when driven by the drive mechanism 136. Relative rotation between the plunger rod 131 and the nut 122 causes the plunger rod 131 to advance axially towards the proximal end 102a of the housing 102. The plunger 133 has a top face 133a that is disposed near the syringe barrel 112.

In the illustrated example, the drive mechanism 136 is in the form of a power spring or a torque spring 136 that is coupled to the rod portion 127 of the plunger rod guide 126 via any known approach to exert a torque on the plunger rod guide 126 that causes the plunger rod guide 126 to rotate about axis L. In some examples, the torque spring 136 may have a high number of turns to provide an appropriate rotational travel required to expel the medicament from the syringe barrel 112, however, additional parameters of the spring design may influence its torque output such as material properties and any applied heat treatments. The pre-shaping of the torque spring 136 may also impact its performance. As an example, in an autoinjector, a pre-stressed spring may be preferred, because the pre-stressing process generally increases torque output of the spring by initial coiling the spring in an opposite direction of the intended working condition, thereby causing permanent deformation in the steel band. This deformation maximizes the stresses in the material, thereby causing the torque to increase. Such an increase in torque is beneficial to minimize device size and weight.

The threaded interface between the plunger rod 131 and the nut 122 provides a translation between the input torque of the torque spring 136 and the output axial force. By providing a torque spring 136 with a high turn count, it will have a lower overall torque as well as a smaller change in start and end torque as compared to a linear spring having comparable gearing specifications or other torsion springs with few turns and a lower pitch. Additionally, the threads of the plunger rod 131 and the nut 122 can have a lower pitch due to the increase in turn count, while still achieving the same linear motion of the plunger rod assembly 130. If the thread pitch is low, a smaller input torque is necessary to provide the same output force as a high pitch thread and high torque spring. Accordingly, the high turn count (e.g., between approximately 1 and approximately 30 turns), low torque system described herein allows for reduced activation forces, as the activation force is directly related to the input torque that must be used to drive the plunger rod assembly 130. Additionally, internal structural forces required to resist the torque from the torque spring 136 during storage (e.g., prior to use) is reduced, thus allowing for smaller injector designs to be used and for less expensive raw materials to be used. Additionally, the threaded interface between the plunger rod 131 and the nut 122 allows the threaded plunger rod 131 to be adjusted to accommodate for varying quantities of medicament stored in the syringe barrel 112. If necessary, the threaded plunger rod 131 may be initially installed at a lower position in injectors 100 having lesser drug product volumes disposed in the syringe barrel 112. Accordingly, the number of unique components is reduced, and variation management is simplified. The threaded plunger rod 131 may also be adjustably installed at various depths during the manufacturing and/or assembly process as needed.

The audible indicator 140 is operably coupled to the drive assembly 120. In this example, the audible indicator 140 is in the form of a ring that at least partially surrounds the plunger rod guide 126, and in particular, surrounds the rod portion 127 of the plunger rod guide 126. The audible indicator 140 includes an engagement portion 144 surrounded by a winged portion or portions 142 that define the ring. The audible indicator 140 may be constructed from any number of materials such as, for example, polymers such as a silicone polymer, metallic materials, composites, and the like. In the illustrated example, the audible indicator 140 is constructed from a resilient material that allows the audible indicator 140 to stretch or elongate in a radial direction.

The engagement portion 144 of the audible indicator 140 is in the form of a block or tab. When the audible indicator 140 is installed (i.e., when the winged portions 142 surround the rod portion 127 of the plunger rod guide 126), the engagement portion 144 is inserted into the slot 129 of the plunger rod guide 126. Accordingly, the audible indicator 140 is at least partially retained by the plunger rod guide 126.

When the engagement portion 144 of the audible indicator 140 is inserted through the slot 129 of the plunger rod guide 126, the engagement portion 144 engages and/or comes into close contact with a portion of the plunger rod 131. In some examples, when the device 100 is in this initial or loaded state (i.e., prior to administration of the medicament 113), the engagement portion 144 of the audible indicator 140 may be nested within or abut against the second detent 135 of the plunger rod 131. In this configuration, the audible indicator 140 is in a generally relaxed state and is minimally stressed.

Generally, to activate the device, a user presses the device 100 against their skin, thereby causing the trigger ring 124 to disengage from the nut 122 and/or the plunger rod guide 126. Such disengagement allows the plunger rod guide 126 to rotate relative to the trigger ring 124. Because the torque spring 136 is in a wound or compressed state, the torque spring 136 will begin to unwind, thereby causing the plunger rod guide 126 to rotate. Due to the threaded interface between the plunger rod 131 and the nut 122, the plunger rod 131 and the plunger 133 advance towards the proximal end 102*a* of the housing 102, thereby inserting the needle or cannula 114 and administering the medicament 113. As a non-limiting example, U.S. Provisional Application No. 62/719,367, filed on Aug. 17, 2018, describes an activation process and components of the drive assembly in further detail and accordingly is incorporated by reference herein in its entirety.

Figure 2A:
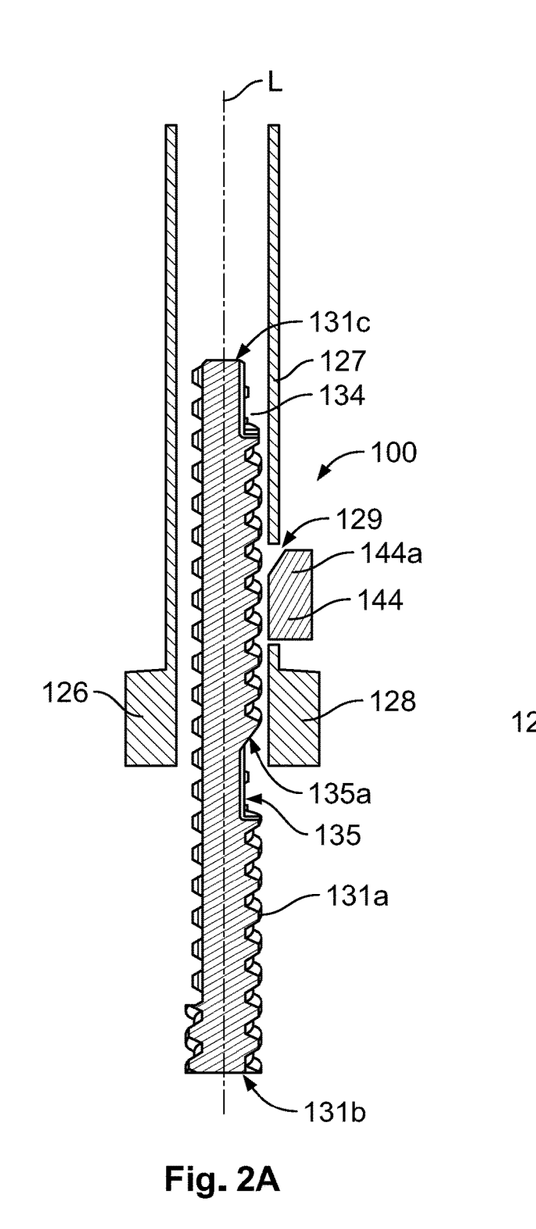
FIG. 2a illustrates a cross-sectional view of the example drug delivery device of FIGS. 1a and 1b during administration of a drug in accordance with various embodiments.
Figure 2B:
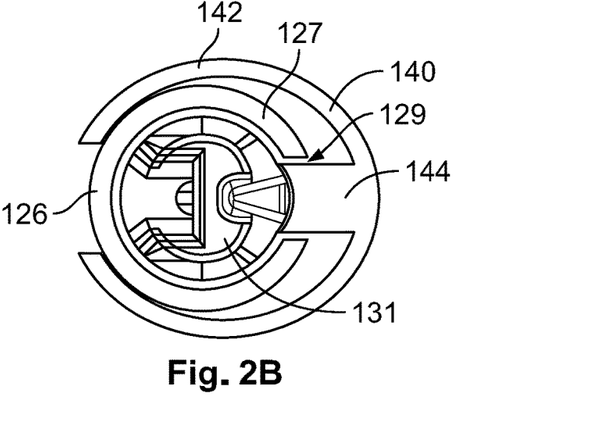
FIG. 2b illustrates a top plan cross-sectional view of a portion of the example drug delivery device of FIG. 2a depicting the audible indicator in a stressed condition in accordance with various embodiments.

Turning to FIGS. 2*a* and 2*b*, delivery of the medicament 113 commences. It should be appreciated that some components of the device 100 are not illustrated in FIGS. 2*a* and 2*b* for the sake of clarity. Upon administration of the medicament 113, the plunger rod 131 moves axially relative to the plunger rod guide 120 and the audible indicator 140. Within a short distance of travel by the plunger rod 131, due to an increase in overall diameter of the plunger rod 131, the threaded portion 131*a* begins to push the engagement portion 144 of the audible indicator 140 outwardly (i.e., in a radial direction). In some examples, the engagement portion 144 includes a chamfered or angled surface 144*a* that corresponds to a chamfered or angled surface 135*a* of the second detent 135 to assist in a smooth outward displacement by the audible indicator 140. In this position, and during administration of the medicament 113, the audible indicator 140 is in a stressed or stretched configuration. Specifically, the winged portion(s) 142 remain coupled to the plunger rod guide 126, but are stretched in an outward configuration relative to the initial, prestressed configuration. Accordingly, the audible indicator 140 stores energy while the plunger rod 131 moves from the initial position towards the second position.

Figure 3A:
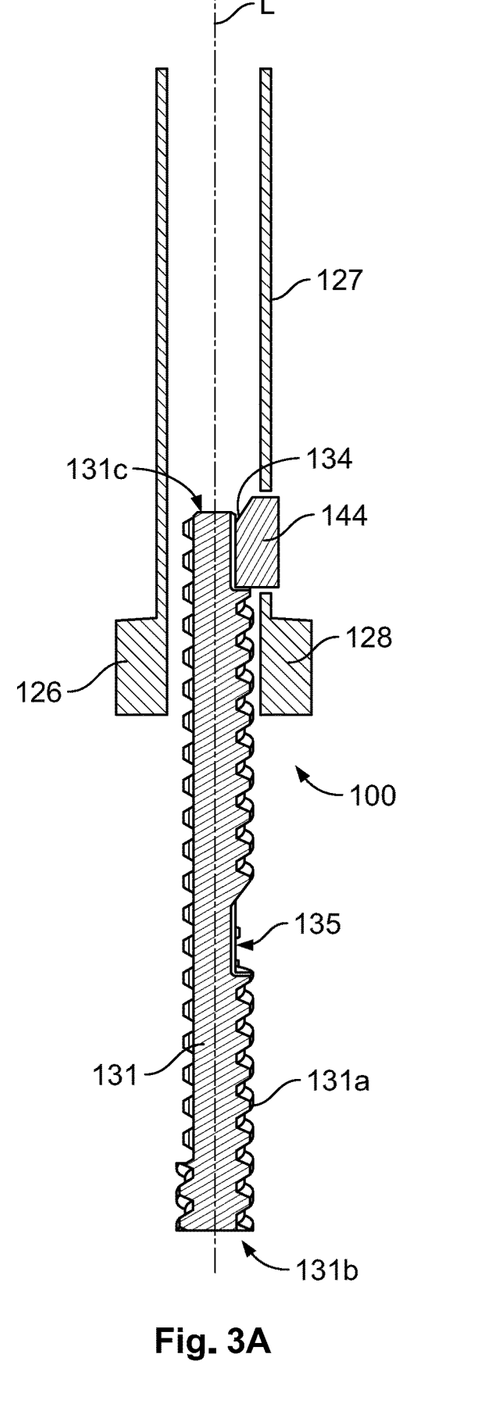
FIG. 3a illustrates a cross-sectional view of the example drug delivery device of FIGS. 1a-2b upon completion of administration of the drug in accordance with various embodiments.
Figure 3B:
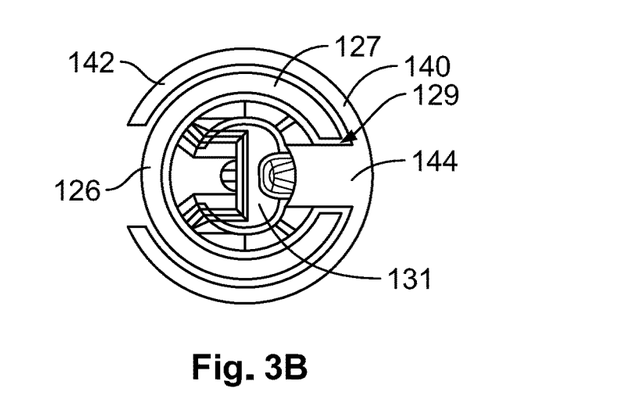
FIG. 3b illustrates a top plan cross-sectional view of a portion of the example drug delivery device of FIG. 3a depicting engagement between the audible indicator and the drive mechanism in accordance with various embodiments.

Turning to FIGS. 3*a* and 3*b*, delivery of the medicament 113 is complete, and the drive assembly 120, specifically the plunger rod 131, is in a second position that results in the medicament 113 being expelled from the syringe 112. When the plunger rod 131 moves to this second position, the first detent 134 allows the audible indicator 140 to move back to its original state and/or position. The engagement portion 144 of the audible indicator 140 engages the first detent 134 of the plunger rod 131, and due to the stored energy in the audible indicator 140, the engagement portion 144 (and in some examples, a portion of the winged portion 142) snaps back into contact with the plunger rod 131 to generate an audible sound such as a click.

In any mechanism where a release of force is necessary, it is important to consider when the force is applied to the mechanism (i.e., when the mechanism is loaded) and how this is done. The audible indicator 140 described herein is not in a loaded state when the device 100 is not in use. Accordingly, it is no longer necessary to consider the relaxation of parts. During the initial activation of the device, the torque spring 136 has the most power and the lowest amount of resistance. The audible indicator 140 is loaded during this initial activation, which is the time when the device 100 is least impacted by the loading.

Figure 4:
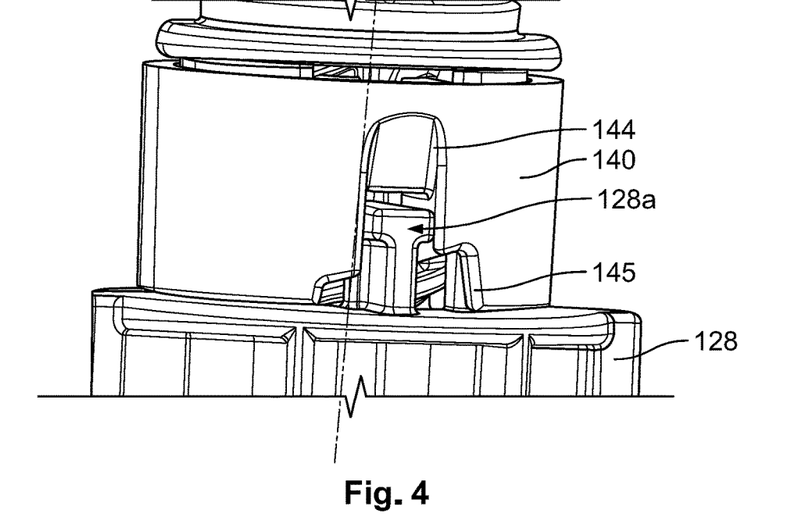
FIG. 4 illustrates a perspective view of a portion of the example drug delivery device of FIGS. 1a-3b in accordance with various embodiments.

Turning to FIG. 4, the plunger rod guide 126 may additionally include a guide feature 128*a* in the form of a tab or key that guides the radial movement of the engagement portion 144 of the audible indicator 140 by engaging a keyhole 145 of the audible indicator 140. The guide feature 128 additionally ensures the audible indicator 140 is correctly oriented in the device 100. This helps to identify assembly errors in production since the part cannot be incorrectly installed.

Figure 5:
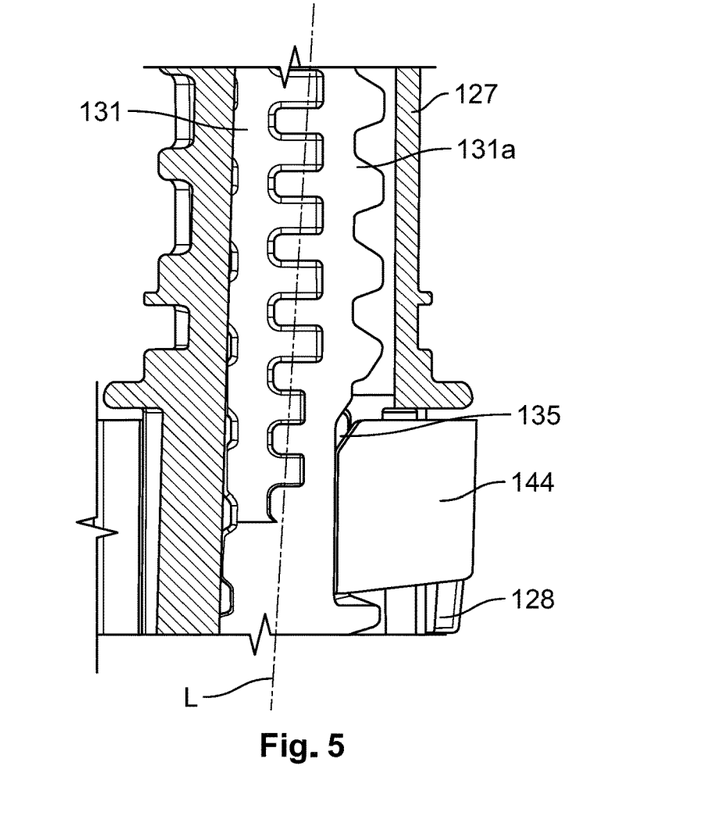
FIG. 5 illustrates a cross-sectional view of the example drug delivery device depicting an engagement between the audible indicator and the drive mechanism in accordance with various embodiments.

As noted, the audible indicator 140 may be constructed from a number of materials. In some examples, the audible indicator 140 is constructed from silicone (e.g., POM+Si/ KEP-TS25H) to reduce friction between it and the plunger rod 131. Additionally, and as illustrated in FIG. 5, during dosing, the audible indicator 140 slides over the threaded portion 131*a* of the plunger rod 131. To ensure the user does not perceive this during use of the device 100, the height of the engagement portion 144 of the audible indicator (illustrated as C1 in FIG. 5) that traverses the threads must be equal to or larger than the distance ("P1") between multiple threads to ensure the engagement portion 144 pushes against more than one thread, thereby reducing any relative wobble the user may experience. Notably, the chamfered surface 144*a* of the engagement portion 144 also smoothly slides across the threaded portion 131*a* of the plunger rod 131.

It should be appreciated that in some examples, when the device 100 is in a loaded state, the audible indicator 140 may be in a partially stressed and/or stretched configuration. However, upon movement of the plunger rod 131 towards the second position, the plunger rod 131 will exert an additional outward or radial force on the audible indicator 140, thereby causing the audible indicator 140 to snap back into the relaxed state upon the engagement portion 144 of the audible indicator 140 when the engagement portion 144 moves from the threaded portion 131*a* of the plunger rod 131 to the first detent 134. Further, it should be appreciated that in some examples, the plunger rod 131 may not include a second detent, and accordingly, the audible indicator 140 may simply remain in a stressed or stretched configuration until the engagement portion 144 of the audible indicator 140 moves into the first detent 134.

In some aspects the volume and tone of the audible sound may be adjusted by modifying the amount of force released, the relative geometries of the components, and/or the freedom of the components to vibrate and/or produce sound.

Figure 6A:
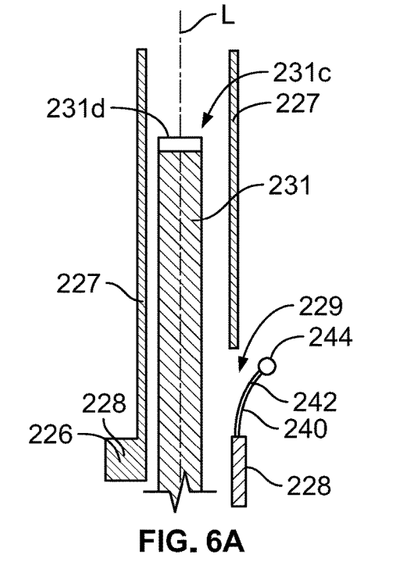
FIG. 6a illustrates a cross-sectional view of a second example drug delivery device in an initial state in accordance with various embodiments.
Figure 6B:
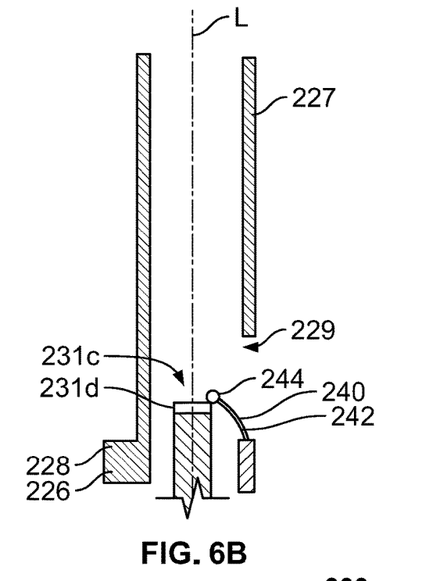
FIG. 6b illustrates a cross-sectional view of the second example drug delivery device in a second state in accordance with various embodiments.

In some examples, the audible indicator may take different forms. Accordingly, FIGS. 6*a* and 6*b* illustrate an alternative audible indicator 240 for a drug delivery device 200. It should be appreciated that the device 200 may include similar and/or identical components as the device 100, and thus, for the sake of brevity, these features are not illustrated and will not be discussed. In this example, the first end 231*c* of the plunger rod guide 231 includes a magnetic member 231*d*. In this example, the audible indicator 240 is in the form of a metallic coupling having a resilient member 242 and a metallic member 244. As illustrated in FIG. 6*a*, in a loaded configuration, the metallic member 244 is positioned away from the plunger rod 231. As illustrated in FIG. 6*b*, upon completion of administration of the medicament, magnetic attraction between the magnetic member 231*d* and the metallic member 244 causes the resilient member 242 to swing inwardly towards the plunger rod 231. Accordingly, the metallic member 244 engages the magnetic member 231*d* thereby generating an audible sound. It should be appreciated that in some examples, the magnetic member may be coupled to the audible indicator, and the first end 231c of the plunger rod 231 may include a metallic member.

In some examples, the audible indicator may be integrally formed with and/or coupled to other components of the device. Accordingly, FIGS. 7a-7d illustrate an alternative audible indicator 340 for a drug delivery device 300. It should be appreciated that the device 300 may include similar and/or identical components as the device 100, and thus, for the sake of brevity, these features are not illustrated and will not be discussed. In this example, the audible indicator 340 is an integral component of the trigger ring 324 and is in the form of a finger or hook protruding therefrom. The plunger rod 331 includes a detent or cutout 335 dimensioned to accommodate the audible indicator 340.

Figure 7A:
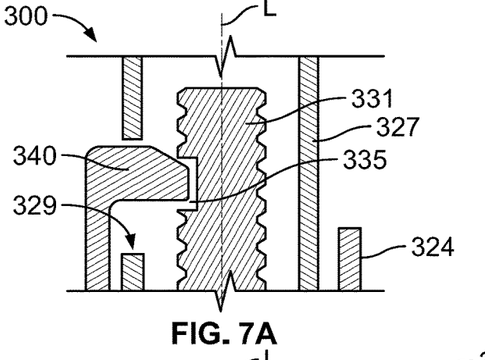
FIG. 7a illustrates a cross-sectional view of a third example drug delivery device in an initial state in accordance with various embodiments.
Figure 7B:
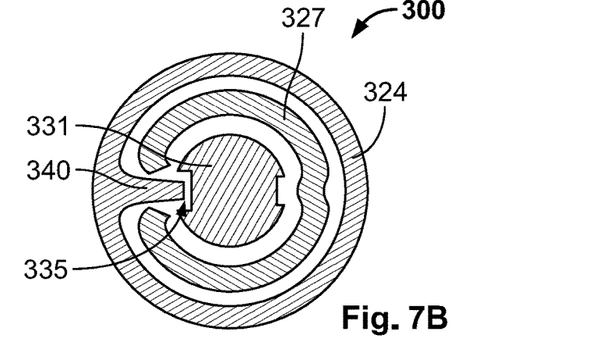
FIG. 7b illustrates a top plan cross-sectional view of a portion of the example drug delivery device of FIG. 7a in accordance with various embodiments.
Figure 7C:
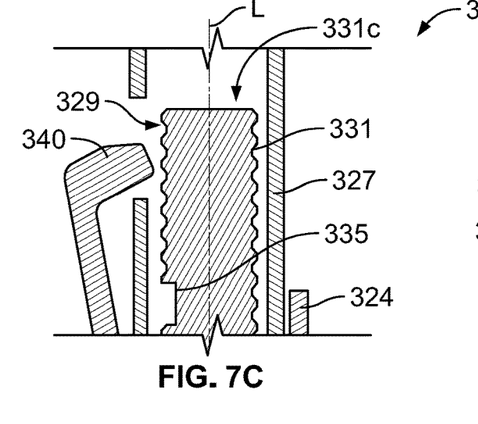
FIG. 7c illustrates a cross-sectional view of the example drug delivery device of FIGS. 7a and 7b in a second state in accordance with various embodiments.
Figure 7D:
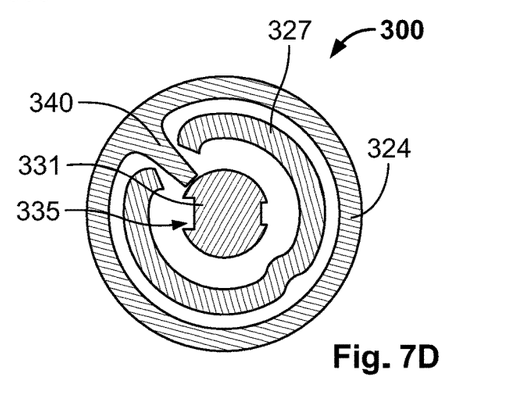
FIG. 7d illustrates a top plan cross-sectional view of a portion of the example drug delivery device of FIG. 7c in accordance with various embodiments.

In an initial configuration or position, and as illustrated in FIGS. 7a and 7b, the audible indicator 340 is disposed within the detent 335, and thus is in a relaxed configuration. In FIGS. 7c and 7d, the device 300 has been actuated, and relative movement begins to occur. First, the trigger ring 324 and/or the plunger rod 331 rotate relative to each other, thereby causing the audible indicator 340 to also rotate and exit the detent 335 and abut against the plunger rod 331, therefore causing the audible indicator 340 to splay outwardly and be loaded with a force. Additionally, relative axial movement along the longitudinal axis L between the trigger ring 324 and the plunger rod 331 occurs in a similar manner as the device 100 previously described in FIGS. 1a-3b. At the end-of-dose, the audible indicator 340 does not engage an additional detent or cutout, but rather snaps or clicks against the second end 331c of the plunger rod 331.

Figure 8A:
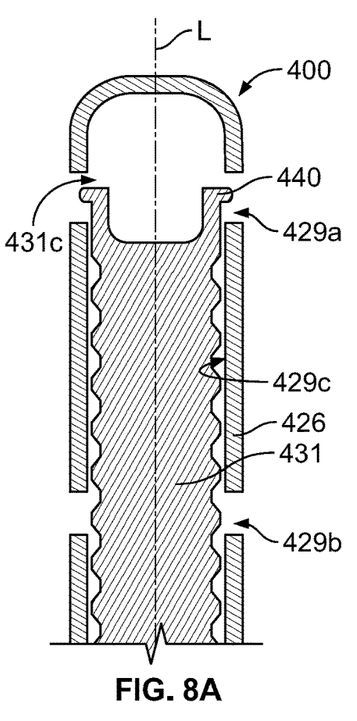
FIG. 8a illustrates a cross-sectional view of a fourth example drug delivery device in an initial state in accordance with various embodiments.
Figure 8B:
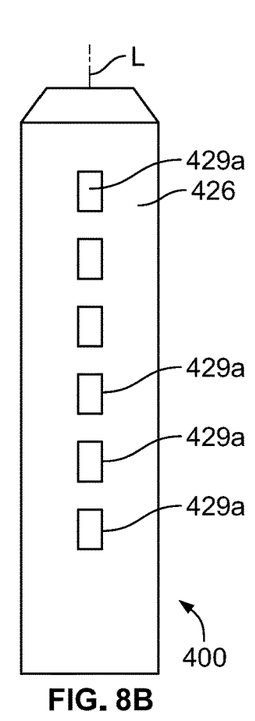
FIG. 8b illustrates a perspective view of a portion of the example drug delivery device of FIG. 8a in accordance with various embodiments.
Figure 8C:
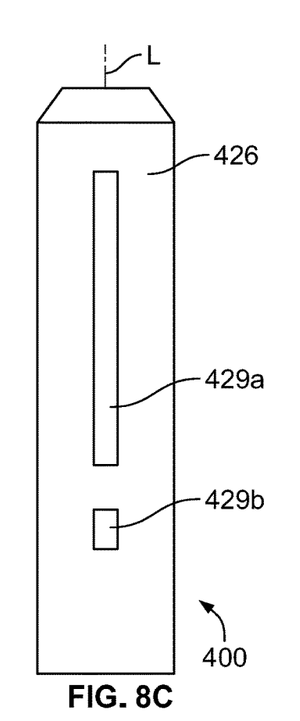
FIG. 8c illustrates a perspective view of an alternative portion of the example drug delivery device of FIG. 8a in accordance with various embodiments.

In some examples, the audible indicator may be integrally formed with and/or coupled to still other components of the device. Accordingly, FIGS. 8a-8c illustrate an alternative audible indicator 440 for a drug delivery device 400. It should be appreciated that the device 400 may include similar and/or identical components as the devices 100, 200, and 300, and thus, for the sake of brevity, these features are not illustrated and will not be discussed. In this example, the audible indicator 440 is an integral component of the plunger rod 431 and is in the form of any number of fingers or hooks protruding from the second end 431c thereof. In this example, the plunger rod guide 426 includes at least a first opening or window 429a and a second opening or window 429b dimensioned to accommodate the audible indicator 440.

In an initial configuration or position, and as illustrated in FIG. 8a, the audible indicator 440 is at least partially disposed within the first opening or window 429a, and thus is in a relaxed configuration. Upon actuation of the device 400, relative axial movement along the longitudinal axis L occurs between the plunger rod guide 426 and the plunger rod 431 causing the audible indicator 440 to displace from the first opening or window 429a and be inwardly splayed and loaded with a force due to contact with an inner surface 429c of the plunger rod guide 426. At the end-of-dose, the audible indicator 440 engages the second opening or window 429b and snaps or clicks against the plunger rod guide 426, thereby generating an audible sound.

As illustrated in FIG. 8b, in some approaches, the plunger rod guide 426 may include any number of additional first windows 429a to allow the plunger rod 431 to be placed at different positions depending on the volume of the medicament being delivered. As illustrated in FIG. 8c, in some approaches, the plunger rod guide 426 may include an elongated first window 429a that accommodates placement of the plunger rod 431 at any number of lengths along a longitudinal axis. The elongated first window 429a illustrated in FIG. 8c advantageously allows the audible indicator 440 to remain in a relaxed configuration during a substantial amount of travel in the longitudinal axis during dosing, and only becomes loaded a short time before the end-of-dose. Other examples are possible.

In some approaches, the audible indicator may be integrally formed with and/or coupled to other components of the device. Accordingly, FIGS. 9a-9d illustrate an alternative audible indicator 540 for a drug delivery device 500. It should be appreciated that the device 500 may include similar and/or identical components as the devices 100, 200, 300, and 400, and thus, for the sake of brevity, these features are not illustrated and will not be discussed. In this example, the audible indicator 540 is an integral component of the plunger rod guide 526 and is in the form of any number of fingers or hooks protruding inwardly therefrom. In this example, the plunger rod 531 includes at least a first cutout or detent 534 and a second cutout or detent 535 dimensioned to accommodate the audible indicator 540.

Figure 9A:
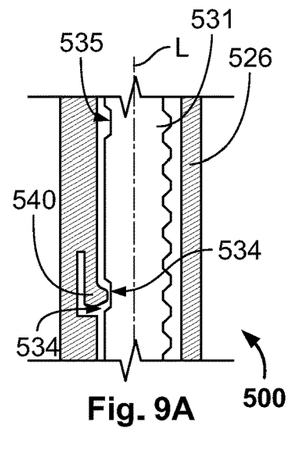
FIG. 9a illustrates a cross-sectional view of a fifth example drug delivery device in an initial state in accordance with various embodiments.
Figure 9B:
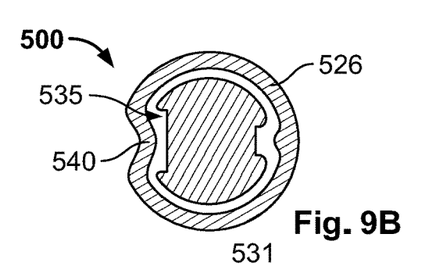
FIG. 9b illustrates a top cross-sectional plan view of a portion of the example drug delivery device of FIG. 9a in accordance with various embodiments.
Figure 9C:
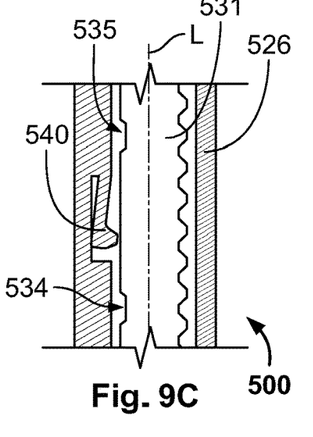
FIG. 9c illustrates a cross-sectional view of the example drug delivery device of FIGS. 9a and 9b in a dosing state in accordance with various embodiments.
Figure 9D:
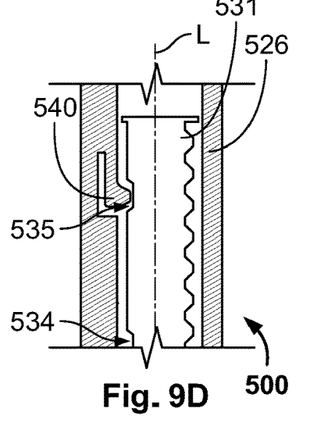
FIG. 9d illustrates a cross-sectional view of the example drug delivery device of FIGS. 9a-9c in an end-of-dose state in accordance with various embodiments.

In an initial configuration or position, and as illustrated in FIGS. 9a and 9b, the audible indicator 540 is at least partially disposed within the first detent 534, and thus is in a relaxed configuration. Upon actuation of the device 500, and as illustrated in FIG. 9c, relative axial movement along the longitudinal axis L occurs between the plunger rod guide 526 and the plunger rod 531, causing the audible indicator 540 to displace from the first detent 534 and be outwardly splayed and loaded with a force due to contact with the plunger rod 531. At the end-of-dose, and as illustrated in FIG. 9d, the audible indicator 540 engages the second detent 535 and snaps or clicks against the plunger rod 531, thereby generating an audible sound.

Figure 10A:
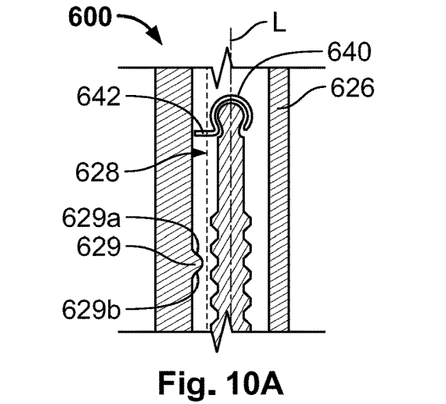
FIG. 10a illustrates a cross-sectional view of a sixth example drug delivery device in an initial state in accordance with various embodiments.
Figure 10B:
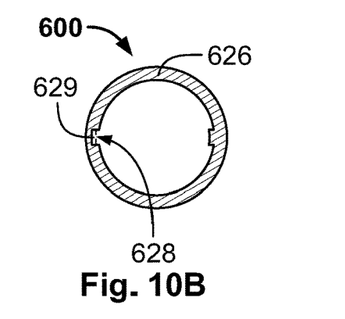
FIG. 10b illustrates a top cross-sectional plan view of a portion of the example drug delivery device of FIG. 10a in accordance with various embodiments.

In FIGS. 10a-10d, an alternative audible indicator 640 for a drug delivery device 600 is provided. It should be appreciated that the device 600 may include similar and/or identical components as the devices 100, 200, 300, 400, and 500, and thus, for the sake of brevity, these features are not illustrated and will not be discussed. In this example, the audible indicator 640 is in the form of a resilient finger 642 that couples to the second end 631c of the plunger rod 631 using any number of approaches. The finger 642 is inserted into a groove 628 formed in the plunger rod guide 626 (as best illustrated in FIG. 10b), thereby allowing the finger 642 to traverse the plunger rod guide 626 in an axial direction along longitudinal axis L. The plunger rod guide 626 further defines a bump 629 having a first surface 629a and a second surface 629b. The bump 629 is disposed within the groove 628.

Figure 10C:
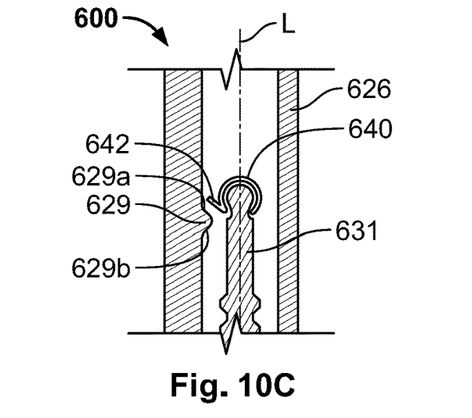
FIG. 10c illustrates a cross-sectional view of the example drug delivery device of FIGS. 10a and 10b in a dosing state in accordance with various embodiments.
Figure 10D:
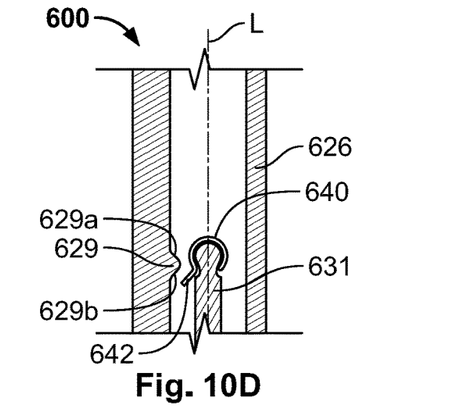
FIG. 10d illustrates a cross-sectional view of the example drug delivery device of FIGS. 10a-10c in an end-of-dose state in accordance with various embodiments.

As illustrated in FIG. 10c, during administration of the medicament, the finger 642 engages the first surface 629a of the bump and displaces upwardly to become loaded with a force. At the end-of-dose, and as illustrated in FIG. 10d, the finger 642 releases from the first surface 629a of the bump 629 and slaps or clicks against the second surface 629b of the bump 629 to generate an audible sound.

Figure 11A:
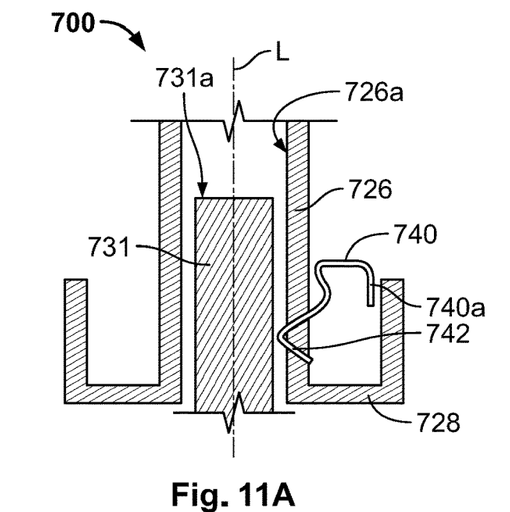
FIG. 11a illustrates a cross-sectional view of a seventh example drug delivery device in an initial state in accordance with various embodiments.
Figure 11B:
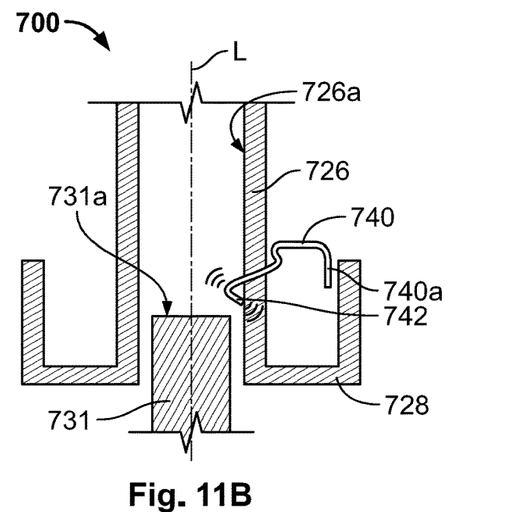
FIG. 11b illustrates a cross-sectional view of the example drug delivery device of FIG. 11 in an end-of-dose state in accordance with various embodiments.

In FIGS. 11a and 11b, an alternative audible indicator 740 for a drug delivery device 700 is provided. It should be appreciated that the device 700 may include similar and/or identical components as the devices 100, 200, 300, 400, 500, and 600, and thus, for the sake of brevity, these features are not illustrated and will not be discussed. In this example, the audible indicator 740 is in the form of a spring having a contact arm 742. The plunger rod guide 726 includes a winged portion 728 to accommodate a first portion 740a of the spring 740. In these examples, the audible indicator 740 is nestled within the winged portion 728, and is naturally disposed in a radially inward direction. While not shown, the audible indicator 740 may be disposed through an opening, slot, and/or notch formed in the plunger rod guide 726 to allow the contact arm 742 to contact the plunger rod 731. When the plunger rod 731 is disposed within the plunger rod guide 726, the plunger rod 731 outwardly displaces the contact arm 742, thereby loading the audible indicator 740 with a force. As illustrated in FIG. 11b, at the end-of-dose, the contact arm 742 of the audible indicator 740 releases from the plunger rod 731 and generates an audible vibration. In some examples, the contact arm 742 of the audible indicator 740 may contact an inner surface 726a of the plunger rod guide 726 to generate a slap or clicking sound.

Advantageously, the described audible indicator provides a clear indication as to when the user can safely remove the device from the injection site. The audible indicator triggers off of the axial position of the plunger rod, thereby ensuring that the audible sound does not occur prematurely, and rather only occurs when the plunger rod has moved a predetermined distance representative of the end-of-dose of the medicament. The mechanism uses minimal additional parts to produce the sound, and the design can ensure correct assembly by only being capable of being installed in one way. In some examples, the first detent or portion the audible indicator engages may not be disposed on the end of the plunger rod. Rather, this detent or cutout may be located at any distance along the plunger rod that is representative of the end-of-dose of the medicament.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number:2 as set forth therein in FIG. 2 and/or the heavy chain of sequence identification number:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers: 305-351, including TN8-19-1 through TN8-19-40, TN8-19 con1 and TN8-19 con2; peptibodies of the mL2 family of sequence identification numberS:357-383; the mL15 family of sequence identification numbers:384-409; the mL17 family of sequence identification numbers:410-438; the mL20 family of sequence identification numbers:439-446; the mL21 family of sequence identification numbers:447-452; the mL24 family of sequence identification numbers:453-454; and those of sequence identification numbers:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published October 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT- 11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences sequence identification number:1 and sequence identification number:7 respectively therein); 5D (having light chain variable and heavy chain variable sequences sequence identification number:2 and sequence identification number:9 respectively therein); 2H (having light chain variable and heavy chain variable sequences sequence identification number:3 and sequence identification number:10 respectively therein); 43H (having light chain variable and heavy chain variable sequences sequence identification number:6 and sequence identification number:14 respectively therein); 41H (having light chain variable and heavy chain variable sequences sequence identification number:5 and sequence identification number:13 respectively therein); and 15H (having light chain variable and heavy chain variable sequences sequence identification number:4 and sequence identification number:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number:17 and the light chain of sequence identification number:18; those having the heavy chain variable region of sequence identification number:6 and the light chain variable region of sequence identification number:8; those having the heavy chain of sequence identification number:19 and the light chain of sequence identification number:20; those having the heavy chain variable region of sequence identification number:10 and the light chain variable region of sequence identification number:12; those having the heavy chain of sequence identification number:32 and the light chain of sequence identification number:20; those having the heavy chain variable region of sequence identification number:30 and the light chain variable region of sequence identification number:12; those having the heavy chain sequence of sequence identification number:21 and the light chain sequence of sequence identification number:22; those having the heavy chain variable region of sequence identification number:14 and the light chain variable region of sequence identification number:16; those having the heavy chain of sequence identification number:21 and the light chain of sequence identification number:33; and those having the heavy chain variable region of sequence identification number:14 and the light chain variable region of sequence identification number:31, as disclosed in the foregoing publication. A specific antibody contemplated is antibody 1119 as disclosed in the foregoing U.S. publication and having a complete heavy chain of sequence identification number:17 as disclosed therein and having a complete light chain of sequence identification number:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number:8 and a light chain variable region having sequence identification number:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX4OL specific antibodies, peptibodies, related proteins, and the like, including but not limited to those described in U.S. Publication No. 2006/0002929, which is incorporated herein by reference in its entirety, particularly in parts pertinent to proteins that bind OX4OL and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim , G-CSF, huMetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507);

Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNa mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
a housing defining a shell having a proximal end and a distal end and a longitudinal axis extending between the proximal end and the distal end thereof;
a needle assembly at least partially disposed within the housing at the proximal end thereof, the needle assembly comprising a syringe containing a medicament and a needle or a cannula;
a drive assembly at least partially disposed within the housing and operably coupled to the needle assembly, the drive assembly including a plunger rod and a plunger rod guide, the plunger rod having a first end and a second end, the drive assembly being movable between an initial position and a second position that results in the medicament being expelled from the syringe; and
an audible indicator operably coupled to the drive assembly, the audible indicator comprising a ring having an engagement tab, the ring including at least one winged portion that at least partially surrounds the plunger rod guide such that upon the drive assembly being positioned in the second position, the audible indicator engages the second end of the plunger rod to generate an audible sound indicating the medicament has been expelled from the syringe.

2. The drug delivery device of claim 1, wherein the audible indicator is adapted to at least partially disengage from the drive assembly upon commencement of movement of the drive assembly from the initial position towards the second position.

3. The drug delivery device of claim 1, wherein the plunger rod further comprises a first detent positioned at the second end.

4. The drug delivery device of claim 3, wherein the plunger rod further comprises a second detent positioned at a distance between the first end and the second end.

5. The drug delivery device of claim 1, wherein the audible indicator is constructed from at least one of a polymer or a metallic material.

6. The drug delivery device of claim 1, wherein the audible indicator is in a relaxed configuration when the drive assembly is in the second position.

7. The drug delivery device of claim 1, wherein the audible indicator is in a relaxed configuration when the drive assembly is in the initial position.

8. A drug delivery device comprising:
a housing defining a shell having a proximal end and a distal end and a longitudinal axis extending between the proximal end and the distal end thereof;
a needle assembly at least partially disposed within the housing at the proximal end thereof, the needle assembly comprising a syringe containing a medicament and a needle or a cannula;
a drive assembly at least partially disposed within the housing and operably coupled to the needle assembly, the drive assembly including a plunger rod having a first end including a magnetic member, the drive assembly being movable between an initial position and a second position that results in the medicament being expelled from the syringe; and
an audible indicator operably coupled to the drive assembly, the audible indicator including a metallic member such that upon completion of delivery of the medicament via the needle assembly, the metallic member of the audible indicator engages the magnetic member of the plunger rod to generate an audible sound indicating the medicament has been expelled from the syringe.

9. The drug delivery device of claim 8, wherein the audible indicator is constructed from at least one of a polymer or a metallic material.

10. The drug delivery device of claim 8, wherein the audible indicator is in a relaxed configuration when the drive assembly is in the second position.

11. The drug delivery device of claim 8, wherein the audible indicator is in a relaxed configuration when the drive assembly is in the initial position.

12. The drug delivery device of claim 1, wherein the syringe is filled or pre-filled with the medicament, and wherein the medicament comprises evolocumab.

13. The drug delivery device of claim 8, wherein the syringe is filled or pre-filled with the medicament, and wherein the medicament comprises evolocumab.

14. A drug delivery device comprising:
a housing defining a shell having a proximal end and a distal end and a longitudinal axis extending between the proximal end and the distal end thereof;
a needle assembly at least partially disposed within the housing at the proximal end thereof, the needle assembly comprising a syringe containing a medicament and a needle or a cannula;
a drive assembly at least partially disposed within the housing and operably coupled to the needle assembly, the drive assembly including a plunger rod and a plunger rod guide, the plunger rod having a first end and a second end, the drive assembly being movable between an initial position and a second position that results in the medicament being expelled from the syringe; and
an audible indicator operably coupled to the drive assembly, the audible indicator comprising a resilient ring having an engagement tab,
wherein, upon the drive assembly being positioned in the second position, the audible indicator engages the second end of the plunger rod to generate an audible sound indicating the medicament has been expelled from the syringe.

15. The drug delivery device of claim 14, wherein the syringe is filled or pre-filled with the medicament, and wherein the medicament comprises evolocumab.

* * * * *